United States Patent
Buechi

(10) Patent No.: US 10,105,511 B2
(45) Date of Patent: Oct. 23, 2018

(54) RESPIRATORY HUMIDIFIER

(71) Applicant: Hamilton Bonaduz AG, Bonaduz (CH)

(72) Inventor: Rudolf Buechi, Chur (CH)

(73) Assignee: Hamilton Medical AG (CH)

( * ) Notice: Subject to any disclaimer, the term of this patent is extended or adjusted under 35 U.S.C. 154(b) by 461 days.

(21) Appl. No.: 14/348,976

(22) PCT Filed: Sep. 27, 2012

(86) PCT No.: PCT/EP2012/069139
§ 371 (c)(1),
(2) Date: Apr. 1, 2014

(87) PCT Pub. No.: WO2013/045586
PCT Pub. Date: Apr. 4, 2013

(65) Prior Publication Data
US 2015/0040897 A1    Feb. 12, 2015

(30) Foreign Application Priority Data
Oct. 1, 2011 (DE) .......................... 10 2011 054 136

(51) Int. Cl.
*A61M 16/10*    (2006.01)
*A61M 16/16*    (2006.01)
(Continued)

(52) U.S. Cl.
CPC ........ *A61M 16/109* (2014.02); *A61M 11/042* (2014.02); *A61M 16/0003* (2014.02);
(Continued)

(58) Field of Classification Search
CPC .............. A61M 16/16; A61M 16/0003; A61M 16/109; A61M 16/108; A61M 16/1085;
(Continued)

(56) References Cited

U.S. PATENT DOCUMENTS

| 4,715,998 A | 12/1987 | Clow |
| 8,006,691 B2 * | 8/2011 | Kenyon ............ A61M 16/0051 122/4 R |

(Continued)

*Primary Examiner* — Todd J Scherbel
*Assistant Examiner* — Elliot S Ruddie
(74) *Attorney, Agent, or Firm* — Jansson Munger McKinley & Kirby Ltd.

(57) ABSTRACT

A respiratory humidifier (1) for a ventilation system is provided, the humidifier comprising:
  a housing (2), which is designed essentially in the shape of an "L" with a horizontal and a vertical part (4, 6) and a projecting portion (10) extending from the free end of the vertical part (6) toward the horizontal part (4), and which comprises a control unit, a user interface (12), and a heating plate (8), wherein the user interface (12) is arranged on the projecting portion (10) and the heating plate (8) is arranged on the horizontal part (4); and
  a liquid container (3), which is designed essentially in the shape of a "U", comprising a recess (7) and a bottom plate (24) as well as two connector elements (5), each of which establishes a connection with a breathing tube;
  wherein the heating plate (8) can be heated for heating the liquid in the liquid container (3), and the bottom plate (24) can be brought into contact with the heating plate (8);
  wherein the liquid container (3) can be slid in such a way onto the housing (2) to establish an operating state so that, when in said operating state, the projecting portion (10) of the housing (2) is positioned above the bottom plate (24) of the liquid container (3).

11 Claims, 4 Drawing Sheets

(51) Int. Cl.
*A61M 16/00* (2006.01)
*A61M 11/04* (2006.01)

(52) U.S. Cl.
CPC ....... *A61M 16/16* (2013.01); *A61M 2205/502* (2013.01); *A61M 2209/086* (2013.01)

(58) Field of Classification Search
CPC .... A61M 2209/086; A61M 2205/5022; A61M 11/042; A61M 16/161; A61M 16/162; A61M 16/164; A61M 16/165; A61M 16/167; A61M 16/168; A61M 16/0069; A61M 16/1075; A61M 16/1095; A61M 16/10; A61M 16/104; A61M 16/1045; A61M 16/14; A61M 16/18; A61M 16/183; A61M 16/186
USPC ............ 128/202.27, 203.16, 203.17, 203.27; 261/101, 104, 129, 142; 392/395, 396
See application file for complete search history.

(56) References Cited

U.S. PATENT DOCUMENTS

| | | | |
|---|---|---|---|
| 8,091,547 B2 * | 1/2012 | Thudor | A61M 16/08 128/203.12 |
| 2006/0113690 A1 | 6/2006 | Huddart et al. | |
| 2006/0237005 A1 * | 10/2006 | Virr | A61M 16/16 128/200.24 |
| 2009/0194106 A1 * | 8/2009 | Smith | A61M 16/0816 128/203.16 |

\* cited by examiner

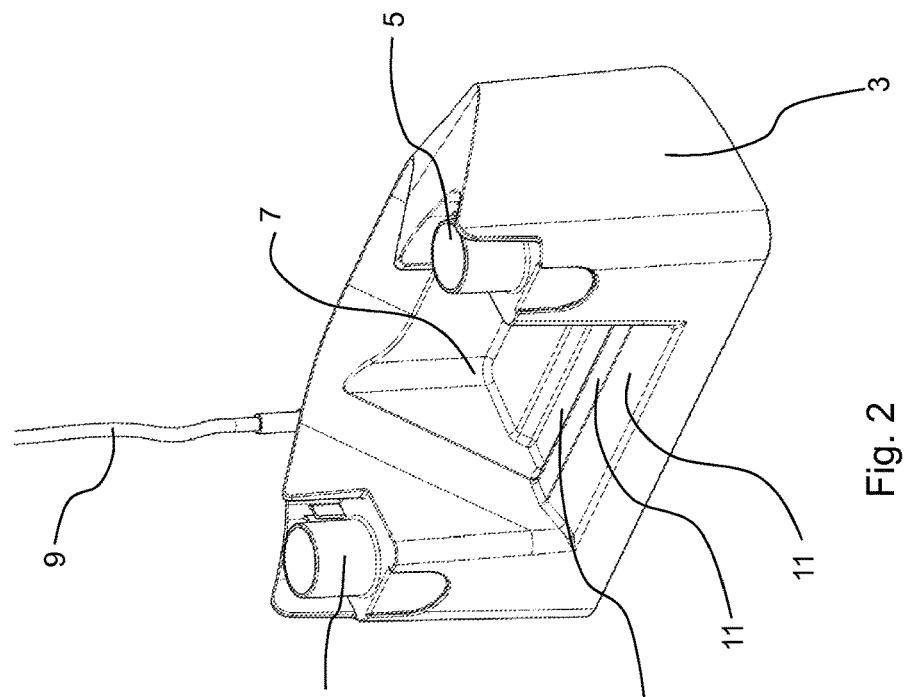
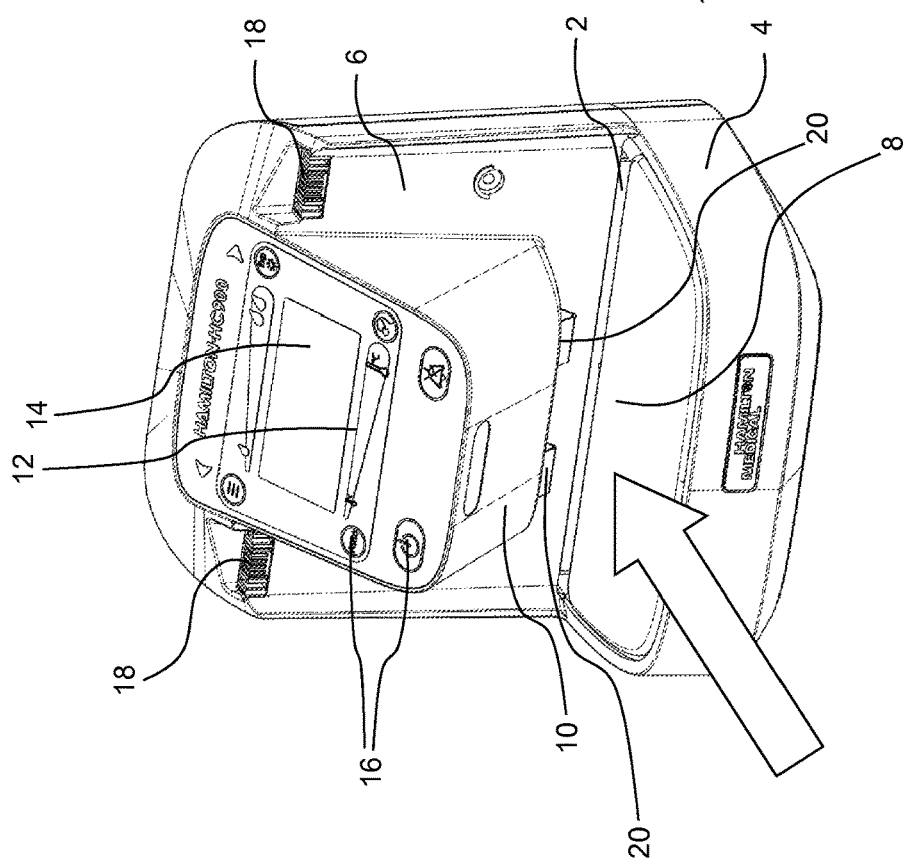

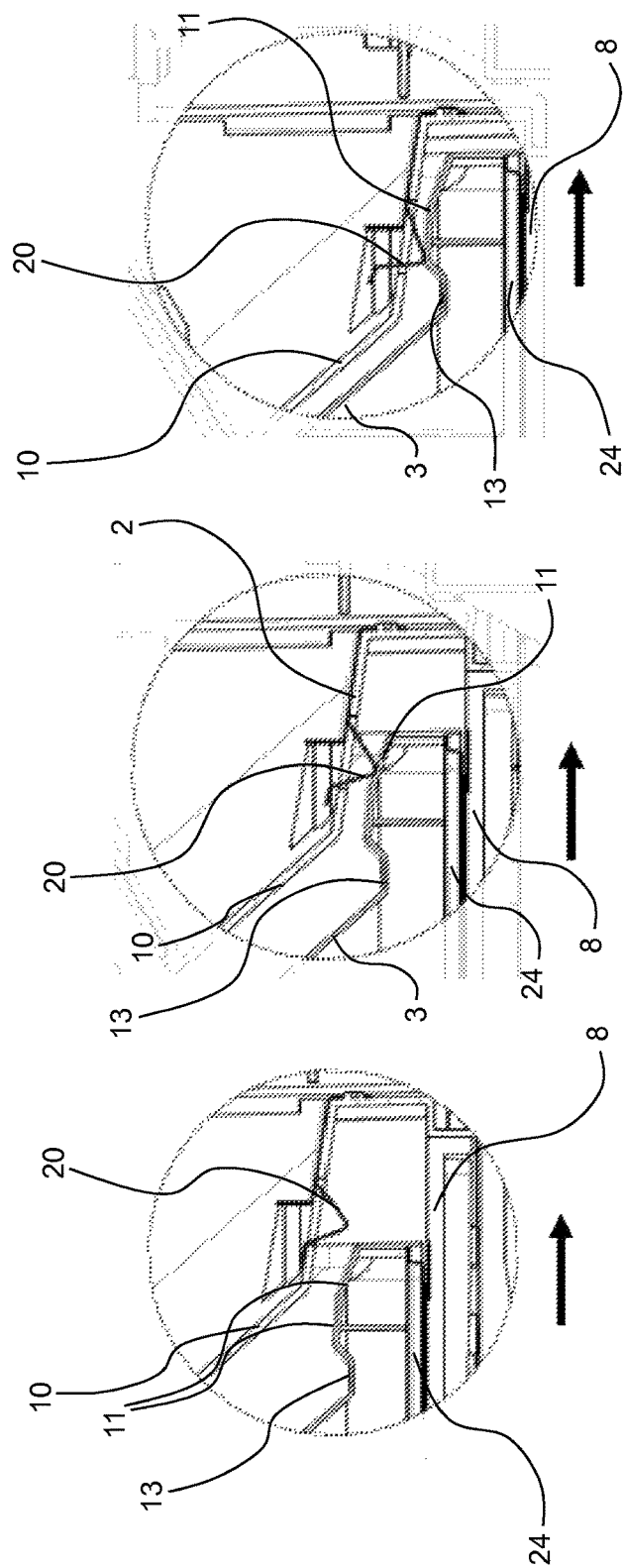

RESPIRATORY HUMIDIFIER

FIELD OF THE INVENTION

The present invention pertains to a respiratory humidifier or respiratory humidifier for a ventilation system.

BACKGROUND OF THE INVENTION

When patients are being mechanically ventilated on an intensive-care ward, for example, the patient to be ventilated is connected pneumatically to the ventilator or respirator by a system of ventilation tubing. Because the breathing air delivered to the patient must be adjusted with respect to temperature and humidity to meet the physiological needs of the patient, a respiratory humidifier or respiratory humidifier is arranged in the inhalation or inspiration tube to heat and humidify the breathing air. The respiratory humidifier comprises a liquid container filled with distilled water, through which the breathing air is conducted and humidified.

The heating of the liquid in the liquid container is usually accomplished by means of a heating plate in the bottom part of the housing of the respiratory humidifier, wherein the heat is transferred from the heating plate to the thermally conductive bottom of the liquid container. The temperature of the breathing air is measured by suitable sensors as it flows in and out, for example, and evaluated so that the respiratory humidifier can be controlled appropriately.

To avoid that the liquid container runs dry or becomes filled with too much liquid, the level of liquid in the container is monitored.

Because, for hygienic reasons, the system of breathing air tubing and the liquid container are designed as medical-grade single-use or disposable articles, two different functional portions are used in a respiratory humidifier. First is the stationary housing, which is connected to the power supply and possibly to other medical devices over a data line; second is the replaceable liquid container, which is usually delivered with the inhalation tubes already attached, so that there is as little chance as possible that the nursing personnel will connect them incorrectly.

The housing and the liquid container must be connected solidly together during operation. In particular, it is absolutely necessary to have good thermal contact between the bottom plate of the liquid container and the heating plate of the housing to ensure adequate heat transfer.

Known respiratory humidifiers with integrated liquid containers, such as that described in US 2006/0113690 A1, also comprise user interfaces, which inform the user about the functional parameters of the respiratory humidifier, for example; and they also have appropriate elements for controlling the operation of the respiratory humidifier. These user interfaces are usually arranged either vertically or horizontally, however, so that they can be seen and operated essentially only from the front or from above. In some cases, they are arranged underneath the liquid container, which means that it is awkward to access them to read or adjust the settings.

Another arrangement of a liquid container in a respiratory humidifier is described in U.S. Pat. No. 4,715,998.

Another disadvantage of the known respiratory humidifiers is that they are relatively large and awkwardly shaped with many corners and edges, for example. They also comprise a large number of connections and contain complicated structural elements. Such devices are therefore complicated to operate, subject to malfunction, and expensive to acquire.

It is therefore the object of the present invention to provide a respiratory humidifier which overcomes the disadvantages cited above and which in particular comprises a user interface which can be operated from the front as well as from above; is simple, ergonomic, and compact in design; and reliably fulfills many different functions.

This object is achieved by the features of claim 1. Advantageous designs and embodiments are described in the subclaims.

SUMMARY OF THE INVENTION

According to an aspect of the invention, a respiratory humidifier for a ventilation system is provided, this humidifier comprising
  a housing, which is designed essentially in the shape of an "L" with a vertical and a horizontal part and a projecting portion extending from the free end of the vertical part toward the horizontal part, and which comprises a control unit, a user interface, and a heating plate, wherein the user interface is arranged on the projecting portion, while the heating plate is arranged on the horizontal part; and
  a liquid container, which is designed essentially in the shape of a "U", comprising a recess and a bottom plate as well as two connector elements, each of which establishes a connection with a breathing tube;
  wherein, to heat the liquid in the liquid container, the heating plate can be heated, and the bottom plate can be brought into contact with the heating plate;
  wherein the liquid container can be slid in such a way onto the housing to establish the operating state so that, when in operation, the projecting portion is positioned above the bottom plate. This design is relatively simple and compact and offers the user the ergonomically advantageous possibility of operating the respiratory humidifier and of inspecting its functional parameters both from above and from the front. Through the elimination of additional or complex elements, the respiratory humidifier is resistant to malfunction; and as a result of the simple sliding mechanism, operator errors are less likely to occur.

When the humidifier is in the operating state, the housing and the liquid container preferably form together an essentially continuous slanted top surface and an essentially continuous lateral surface of the respiratory humidifier, wherein the user interface is integrated into the slanted top surface. This makes the humidifier user-friendly, because, except for the connector elements, there are no large openings in the compact, easily stored unit.

It is especially advantageous for the housing to comprise first fastening means and for the liquid container to comprise second fastening means, wherein the sliding of the liquid container onto the housing brings about engagement between the first and the second fastening means in such a way that the bottom plate is pressed from above onto the heating plate. Because complete thermal and possibly also electrical contact between the heating plate and the bottom plate is essential to the proper functioning of the respiratory humidifier, the bottom plate must be pressed in some way onto the heating plate and held in that position. This is guaranteed by the engagement between the first and second fastening means. A fastening design of this type is simple and works without any complicated mechanisms on the heating plate such as those known from the prior art.

It is advantageous for the first fastening means to be arranged in the bottom area of the projecting portion. It is less in the way there, is protected from manipulations, and is almost invisible to the user.

It is also preferred that it be possible to slide the liquid container onto the housing in a direction essentially parallel to the heating plate.

It is also advantageous for the engagement between the first and second fastening means to be established by a releasable latching mechanism. This latching mechanism is simple and works without any additional fasteners which would have to be operated by the user. It is thus a simple matter to replace the liquid container, which is usually designed as a single-use/disposable article.

It is advantageous for the latching mechanism to be a tongue-and-groove mechanism, wherein the first fastening means comprises at least one tongue, and the second fastening means comprises at least one groove. The housing comprises for this purpose in advantageous fashion at least one opening, through which the at least one tongue projects downward from the housing. A design of this type is extremely simple mechanically, almost invisible from the outside, and not visible at all to the user when the respiratory humidifier is in operation.

It is advantageous for the at least one tongue to be designed as a one-piece spring plate element. Spring steel sheet material for spring plates is low in cost and easy to bring into the desired shape. In addition, it offers a solid and almost failure-proof spring function, which contributes to the long life of the respiratory humidifier.

The liquid container preferably comprises a gripping device in the forward area, facing away from the vertical part of the housing. As a result, the user sees intuitively how the liquid container is to be removed from the stationary housing, and the user will also use the grip when sliding the container back onto the housing. The gripping device is preferably designed as a recess in the front part of the lateral surface of the liquid container and thus represents the only part of the lateral surface of the respiratory humidifier which is not continuous. This means again that the user is guided intuitively to use this grip in order to remove the liquid container from the fixed housing and to slide it back into place again.

It is also preferable for the user interface of the respiratory humidifier to comprise display elements and operating elements. The functions of the respiratory humidifier and possibly of other units of the ventilation system can be displayed on the user interface and also controlled from it. All of the functional components of the respiratory humidifier according to the invention which the user can manage in some way or other while the humidifier is in operation are therefore accessible from the top surface of the respiratory humidifier. This also applies in particular to the connector elements for the ventilation tubes and the refill tube.

It is also advantageous to provide at least one port for the power supply, for data communications, etc., on the back of the vertical part of the respiratory humidifier. The at least one port is advantageously designed in such a way that it does not project beyond the essentially continuous lateral surface of the respiratory humidifier. The external surfaces of the respiratory humidifier thus offer no obstructing projections which could interfere with the positioning of the overall device or which could make the device more difficult to store. This also applies to the situation in which the liquid container is not installed in the device.

BRIEF DESCRIPTION OF THE DRAWINGS

The invention is explained in detail below on the basis of exemplary embodiments with reference to the attached figures:

FIG. 1 shows a perspective view of a housing of a preferred embodiment of the respiratory humidifier according to the invention;

FIG. 2 shows a perspective view of a liquid container of a preferred embodiment of the respiratory humidifier according to the invention;

FIGS. 5-9 show the latching mechanism of the preferred embodiment of the respiratory humidifier according to the invention in different positions of the liquid container.

DETAILED DESCRIPTION

Figure 4:
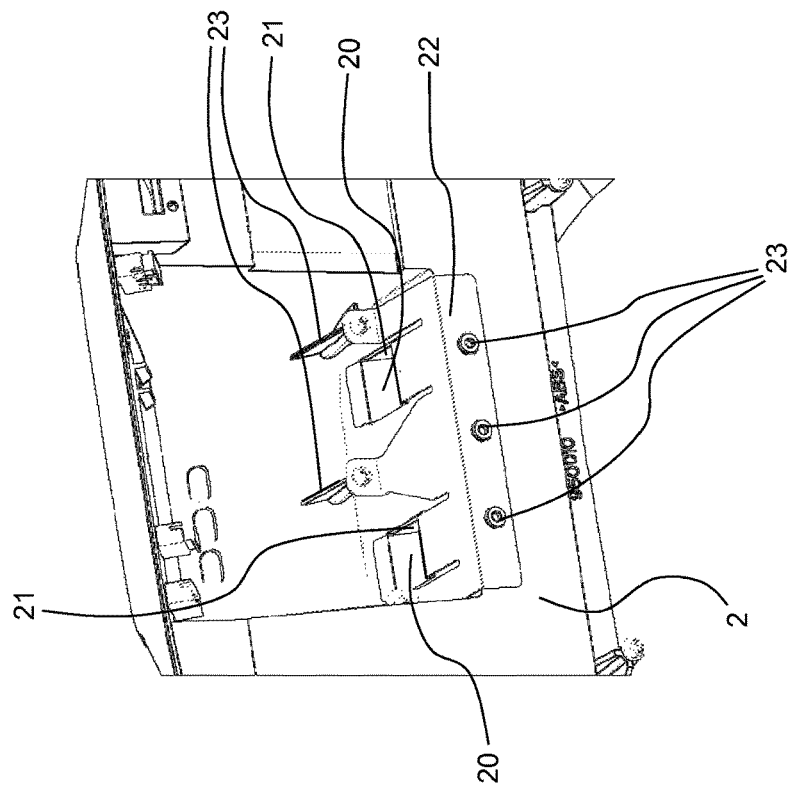
FIG. 4 shows a perspective view of a detail of the housing of the respiratory humidifier according to the preferred embodiment.

FIG. 1 shows a perspective view of the housing 2 of a preferred embodiment of the respiratory humidifier according to the invention. The housing 2 comprises essentially an L-shape with a horizontal part 4 and a vertical part 6. On the horizontal part 4, a heating plate 8 is arranged, which is oriented essentially horizontally and which covers almost the entire upward-facing surface of the horizontal part 4. A projecting portion 10 extends from approximately the middle of the upper, free end of the vertical part 6, wherein the surface of the projecting portion 10 comprises a user interface 12. The user interface 12 comprises a display device 14 and operating elements 16, by means of which the respiratory humidifier can be monitored and controlled. Electrical contact elements 18 are arranged at the upper end of the vertical part 6, offset laterally from the projecting portion 10; these elements can be brought into electrical contact with corresponding connecting parts of a ventilation tubing system. At the bottom end of the projecting portion 10, two spring elements 20 are arranged, each of which projects downward out of an opening (not visible in FIG. 1).

FIG. 2 shows a perspective view of a liquid container 3 of the preferred embodiment of the respiratory humidifier according to the invention. In the upper area, the liquid container 3 comprises two connector elements 5, which are designed as tubular sockets with a circular cross section for establishing pneumatic connections with a breathing tube system. Between the two connector elements 5, the liquid container 3 comprises a recess or cut-out area 7. Furthermore, a refill tube 9 is arranged on the top of the liquid container 3. The bottom of the liquid container 3 (not visible in FIG. 2) is designed as a bottom plate of aluminum. In the lower area of the recess 7, several parallel support surfaces 11 are formed, which are themselves parallel to the direction of a straight line between the two connector elements 5; these support surfaces form a groove 13 approximately in the middle of the lower area of the recess 7. This groove is perpendicular to a fastening device of the liquid container 3.

Figure 3:
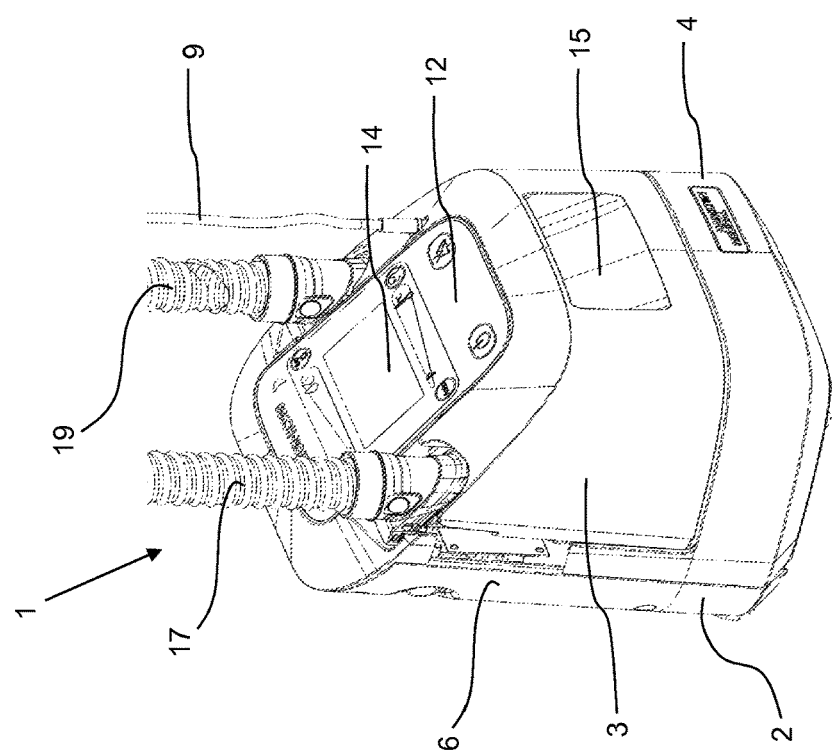
FIG. 3 shows a perspective view of the preferred embodiment in the operating state of the respiratory humidifier according to the invention.

FIG. 3 shows a perspective view of a respiratory humidifier 1 according to the preferred embodiment of the invention in the operating state. The liquid container 3 has been slid into its final position on the housing 2. It can be seen that the top surface of the liquid container 3 and the user interface 12 form an essentially continuous top surface of the respiratory humidifier 1, which is interrupted only by the plugged-in ventilation tubes 17, 19. Also visible in FIG. 3 is the grip 15 on the front portion of the liquid container 3, which can be grasped to slide the liquid container 3 onto the respiratory humidifier 1 or to remove it correspondingly.

FIG. 4 shows a perspective view of a detail of the housing of the preferred embodiment of the respiratory humidifier according to the invention, wherein the focus of this figure is on the first fastening means, which is arranged on the inside in the lower area of the projecting portion 10 in the interior of the housing 2. The first fastening means is designed as a spring plate 22, which is attached by several fastening elements 23 to the housing 2 and comprises two spring tabs 20, each essentially in the shape of a "V", which project downward on the inside, each one through an opening 21 in the housing 2. The ends of the spring tabs 20 are freely exposed, so that it is possible for the liquid container 3 to push the V-shaped portions upward from below into the interior space of the housing 2. When this is done, the V-shaped spring tabs 20 become latched in the groove 13, which can be seen in FIG. 2, for example. In the preferred embodiment, the first fastening means comprises two spring tabs. It should be noted, however, that only one spring element or more than two spring elements can be used, nor do these elements have to be formed integrally out of a single piece of spring plate.

The latching mechanism of the preferred embodiment of the respiratory humidifier according to the invention will now be described on the basis of FIGS. 5-9. FIG. 5 shows a detailed view, in cross section, of the starting position present when the liquid container 3 is ready to be slid into the housing 2. In the lower part, one can see the heating plate 8, onto which the bottom plate 24 of the liquid container is slid and to which it is eventually thermally and electrically coupled. The support surfaces 11 of the liquid container 3 come into contact first with the one or more spring tabs 20, which, when in the relaxed state, project out from the opening 21 into the intermediate space between the projecting portion 10 and the heating plate 8.

FIG. 6 shows the liquid container 3 after it has been slid further into the housing 2. The arrow pointing toward the right in FIGS. 5-8 shows the direction of the sliding action. It can be seen that the spring tab 20 is in contact with the support surface 11, which is arranged at an angle relative to the bottom plate 24 and which thus, as the liquid container 3 moves to the right, pushes the spring tab 20 upward against its elastic force into the opening 21.

FIG. 7 shows the position of the liquid container 3 after it has been slid even farther to the right from the position of FIG. 6. The spring tab 20 has now been bent upward to its maximum deflection into the interior of the projecting portion 10 and rests on the essentially horizontal support surface 11.

Figure 8:
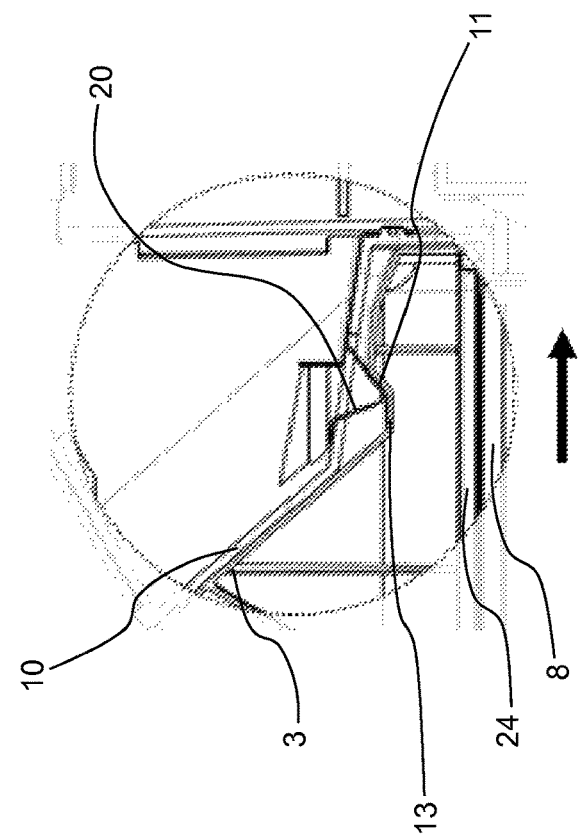

As the liquid container 3 is slid further toward the right, the final position shown in FIG. 8 is finally reached. The spring tab 20 is now somewhat more relaxed than it was when in the position shown in FIG. 7, because it has slipped down along another support surface 11, which leads downward at an angle toward the groove 13. The groove 13 and the corresponding support surface 11 now positively engage the spring tab 20, which is still exerting residual pressure on the groove 13 and thus on the liquid container 3, so that the bottom plate 24 of the liquid container 3 is pressed onto the heating plate 8 and can be released again only by the application of a previously determined releasing force on the liquid container 3.

Figure 9:
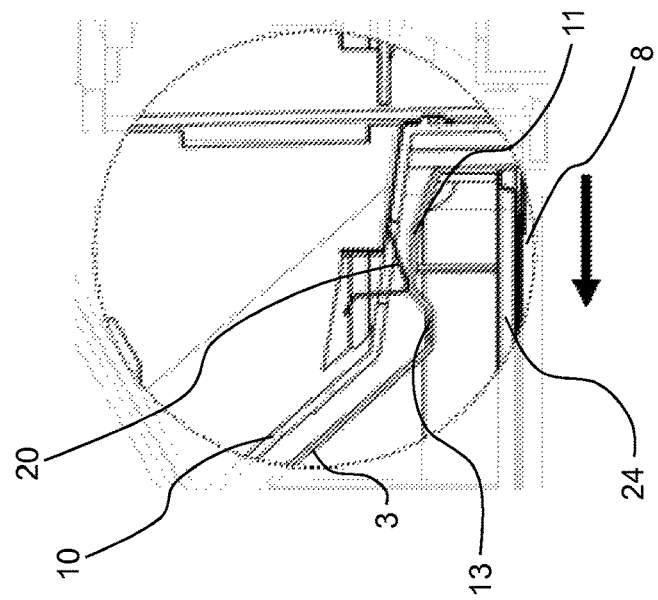

FIG. 9 shows the liquid container 3 in a position in which the elastic force of the spring tab 20 has already been essentially overcome, because the liquid container 3 has been pulled a considerable distance out of the housing 2 by means of the grip 15 (arrow pointing toward the left). Here, too, it can be seen that the spring tab 20 has been pushed upward into the interior of the projecting portion 10 against its elastic force. The person skilled in the art will understand that pulling the liquid container 3 even farther out of the housing 2 will have the effect of releasing the spring element completely, in which state it is no longer engaged with the surface of the liquid container 3.

Within the scope of this invention, it is also possible to conceive of other mechanisms and designs such as magnets instead of the tongue-and-groove design with a spring plate to realize the first and second fastening means.

The subject matter of the present invention provides a respiratory humidifier which is simple and compact in design, comprises a user interface which can be operated from above and possibly also from the front, and which satisfactory fulfills many different functions.

The invention claimed is:

1. A respiratory humidifier for a ventilation system comprising:
    an L-shaped housing including (a) a horizontal part that has a heating plate in fixed position thereon, (b) a vertical part, and (c) a projecting portion that extends from the free end of the vertical part toward the horizontal part and has a control unit, a user interface, and an underside spaced directly over the heating plate;
    a liquid container substantially in the shape of a "U", the liquid container forming a recess configured to receive the projecting portion and having (a) a lower horizontal containment portion defined by a bottom plate for contact with the heating plate and a substantially horizontal upper surface spaced above the bottom plate in position immediately below the underside of the projecting portion and (b) two connector elements each adapted to establish a connection with a breathing tube, the liquid container and housing being configured such that the liquid container can be slid onto the housing to establish an operating state with the projecting portion above the lower horizontal containment portion of the liquid container; and
    at least one first spring-loaded fastener on the underside of the projecting portion, the liquid container having at least one second fastener on the upper surface of the lower horizontal containment portion for engagement with the at least one first spring-loaded fastener at a position spaced above the bottom plate and the heating plate, the first and second fasteners being configured and arranged such that, after sliding the container onto the housing, such engaged fasteners (1) bias the bottom plate down onto the fixed heating plate and (2) hold the container and housing in engagement.

2. The respiratory humidifier of claim 1 wherein, when the humidifier is in the operating state, the housing and the liquid container together form a substantially continuous slanted top surface and a substantially continuous lateral surface of the respiratory humidifier, with the user interface integrated into the slanted top surface.

3. The respiratory humidifier of claim 1 wherein the liquid container is slideable onto the housing in a direction substantially parallel to the surface of the heating plate.

4. The respiratory humidifier of claim 1 wherein the engagement occurs by means of a releasable latching mechanism.

5. The respiratory humidifier of claim 4 wherein the latching mechanism is a tongue-and-groove mechanism, the second fastener(s) having at least one groove.

6. The respiratory humidifier of claim 5 wherein the housing forms at least one opening through which the at least one spring-loaded fastener projects downward out of the housing.

7. The respiratory humidifier of claim 6 wherein the at least one spring-loaded fastener is a one-piece spring plate element.

8. The respiratory humidifier of claim 1 wherein the liquid container includes a gripping device in the forward area facing away from the vertical part of the housing.

9. The respiratory humidifier of claim 1 wherein the user interface includes display elements and operating elements.

10. The respiratory humidifier of claim 1 wherein the rear of the vertical part includes at least one port for a power supply or for data communication.

11. The respiratory humidifier of claim 10 wherein the at least one port is formed to not project beyond the essentially continuous lateral surface of the respiratory humidifier.

* * * * *